United States Patent
Lang et al.

(10) Patent No.: US 6,248,912 B1
(45) Date of Patent: Jun. 19, 2001

(54) ORGANOMETALLIC COMPOUNDS

(75) Inventors: Heinrich Lang, Chemnitz-Harthau; Thomas Weiss, Mannheim-Feudenheim; Sigurd Becke, Rösrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/258,557

(22) Filed: Feb. 26, 1999

(30) Foreign Application Priority Data

Mar. 4, 1998 (DE) ............................... 198 09 159

(51) Int. Cl.$^7$ ............................. C07F 17/00; C07F 7/00; C08F 4/64; B01J 31/00
(52) U.S. Cl. .............................. 556/11; 556/12; 556/20; 556/43; 556/53; 556/54; 526/160; 526/943; 502/103; 502/117
(58) Field of Search ..................... 556/11, 12, 20, 556/43, 53, 54; 526/160, 943; 502/103, 117

(56) References Cited

U.S. PATENT DOCUMENTS 4,404,344  9/1983  Sinn et al. ....................... 526/160

(List continued on next page.)

FOREIGN PATENT DOCUMENTS 277 003  8/1988  (EP) . ............................. (EP) .

(List continued on next page.)

OTHER PUBLICATIONS

Organometallics, (month unavailable) 1993, 12, pp. 5012–5015.

(List continued on next page.)

Primary Examiner—Porfirio Nazario-Gonzalez
(74) Attorney, Agent, or Firm—Joseph C. Gil; Noland J. Cheung

(57) ABSTRACT

Organometallic compounds of transition metals containing optionally tetrahydrogenated 2-indenyl as a first ligand of the formula

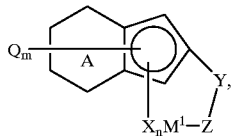

(I)

wherein A represents the benzo system or the tetrahydrocyclohexyl system and the other symbols have the range of meanings given in the description, are prepared by reaction of

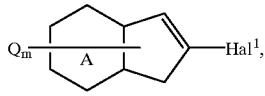

(II)

with Mg or Zn and with a dihalide $Hal^2—Y—Hal^3$ (III) to form the novel intermediates

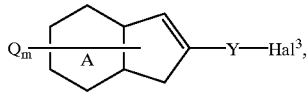

(IV)

further reaction with $ZM^2_p$(Va) or $ZR^0_p$(Vb) to form

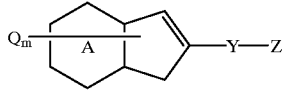

(VII)

and further reaction with a transition metal compound of the formula $M^1X_q$(VIII).

Many compounds (I) are not C2-symmetrical.

The compounds (I) can be used as catalysts for the (co)polymerization of olefins, diolefins and/or cycloolefins.

15 Claims, 1 Drawing Sheet

U.S. PATENT DOCUMENTS

| | | | |
|---|---|---|---|
| 4,542,199 | 9/1985 | Kaminsky et al. | 526/160 |
| 5,026,798 | 6/1991 | Canich | 526/127 |
| 5,132,380 | 7/1992 | Stevens et al. | 526/126 |
| 5,145,819 | 9/1992 | Winter et al. | 502/117 |
| 5,276,208 | 1/1994 | Winter et al. | 556/53 |
| 5,646,322 | 7/1997 | van Beek et al. | 556/11 |
| 5,703,187 | 12/1997 | Timmers | 526/282 |

FOREIGN PATENT DOCUMENTS

| | | |
|---|---|---|
| 277 004 | 8/1988 | |
| 129 368 | 7/1989 | (EP) . |
| 96/13529 | 5/1996 | (WO) . |
| 98/06728 | 2/1998 | (WO) . |

OTHER PUBLICATIONS

Organometallics, (month unavailable) 1997, 16, pp. 3044–3050.

Journal of Organometallic Chemistry, vol. 541, (month unavailable) 1997, Huttenloch et al, pp. 219–232.

ORGANOMETALLIC COMPOUNDS

FIELD OF THE INVENTION

The present invention relates to a process for the preparation of organometallic compounds of transition metals having an indenyl ligand bonded in the 2-position, to such compounds themselves, and to their use as catalysts for the (co)polymerization of olefinic and/or diolefinic monomers. Many of those compounds are not C2-symmetrical.

BACKGROUND OF THE INVENTION

The use of organometallic compounds having two ligands which are or contain the cyclopentadienyl anion as catalysts for the polymerization of olefinic and/or diolefinic compounds is already known (sandwich metallocenes, see EP 35,242, EP 69,951, EP 129,368, EP 277,003, EP 277,004).

It is also known to use organometallic compounds having only one cyclopentadienyl anion as catalysts (semi-sandwich catalysts, see U.S. Pat. No. 5,132,380, EP 416,815, WO 91/04257, WO 96/13529). Semi-sandwich catalysts having an indenyl ligand bridged in the 2-position have not hitherto been known.

Biscyclopentadienyl metal complexes that have a bridge between the two cyclopentadienyl ligands are called ansa-metallocenes. The particular metallocenes include the bis-indenyl metallocenes bridged in the 1-position on the indenyl ligand. Such chiral ansa-metallocene derivatives are especially suitable as catalysts for the preparation of olefin polymers having a high degree of isotaxy, a narrow molecular mass distribution and a high molecular mass, as is described, for example, in EP 485,821 and EP 485,823.

Comparatively little is known about metallocenes having indenyl ligands bridged in the 2-position. Organometallics 1997, 16, 3044–3050 describes an ansa-bisindenylhafnium complex in which one of the indenyl ligands is bridged in the 2-position (dimethylsilyl-(1-indenyl)(2-indenyl)-bis-dimethylamidohafniium, further reaction to dimethylsilyl-(1-indenyl)(2-indenyl)-dimethylhafnium). The metal complex is formed as a by-product in a low yield in a specific process (vacuum, 160° C.) and must be purified in a complicated process. In Organometallics 1993, 12, 5012–5015, a multi-step method of synthesizing ethylenebis(2-indenyl)-titanium dichloride is described. On account of the multi-step synthesis and the numerous purification operations, the yield that can be achieved is very low. Owing to the method of synthesis, the structural variety is restricted to ethylene-bridged ligands. WO 94/11406 discloses organometallic compounds of transition metals which have an indenyl ligand and a cyclopentadienyl ligand, the indenyl ligand being substituted in the 2-position; that substituent may also be in the form of a bridge to the second ligand. The Examples show multi-step preparations with extremely unsatisfactory yields which, in the case of bridged compounds, lead to 1-cyclo-pentadienyl-2-(2-indenyl)-ethane-zirconium chloride, to bis-(2-indenyl)-methane-zirconium dichloride or to dimethylbis-(2-indenyl)-silane-zirconium dichloride, which still contains impurities. In EP 372,414, the two compounds ethylene-1-((3-but-3-enyl)inden-1-yl)-2-((1-but-3-enyl)-inden-2-yl)zirconium dichloride and ethylene-1-((3-allyldimethylsilyl)-inden-1-yl)-2-((1-allyldimethylsilyl)-inden-2-yl)zirconium dichlorides are mentioned.

Owing to the poor availability of organometallic compounds of transition metals having an indenyl ligand bridged in the 2-position, little is known about their use or their catalytic activity.

SUMMARY OF THE INVENTION

It has now been found that organometallic catalysts whose bridging begins at the 2-position of at least one indenyl anion have particular properties as polymerization catalysts in that, in the (co)polymerization of x-olefins, they produce largely atactic polymers having high molecular weights. It was, therefore, desirable to find a preparation process for such catalysts bridged in the 2-position of at least one indenyl anion.

DETAILED DESCRIPTION OF THE INVENTION

Figure 1:
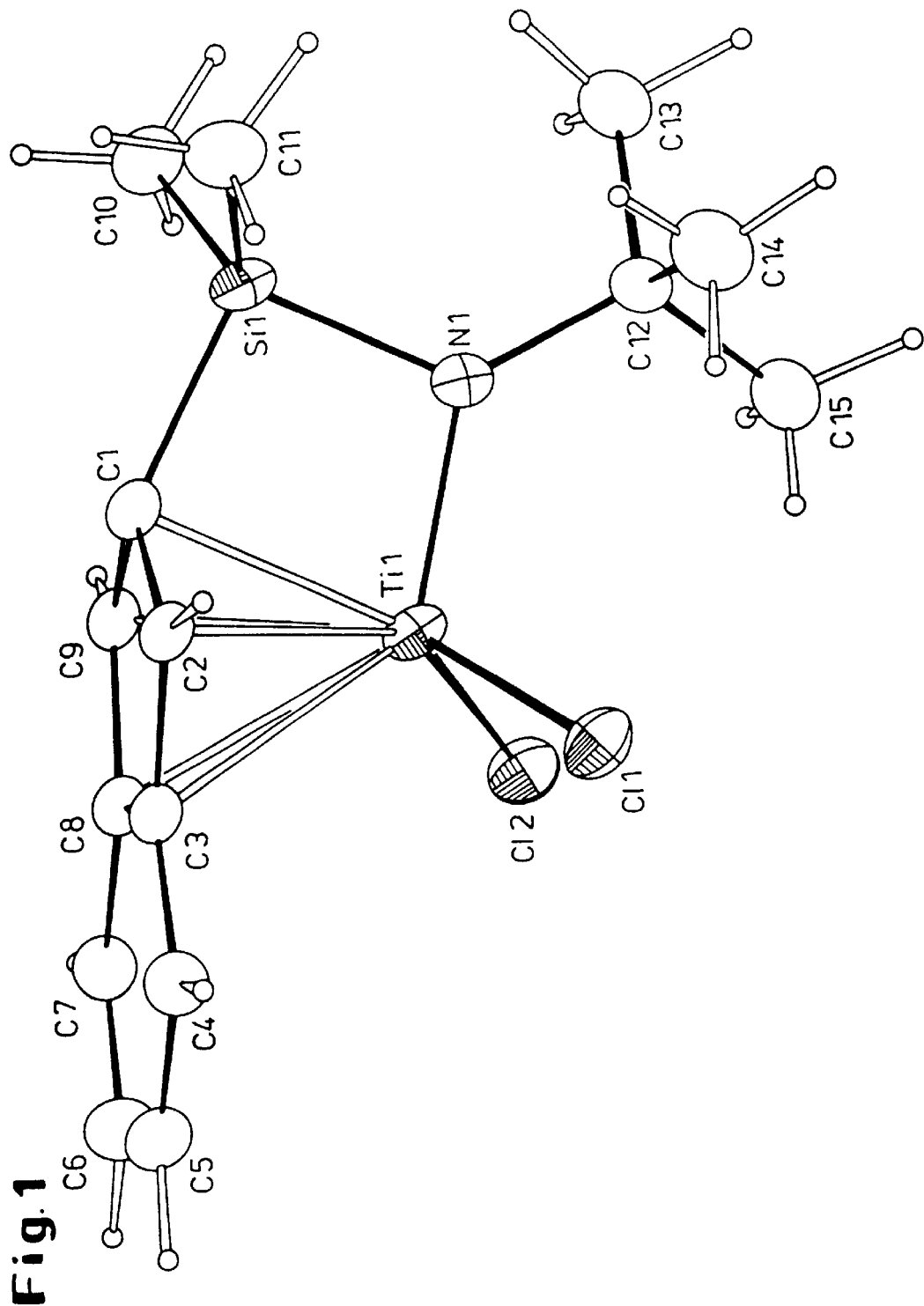
FIG. 1 shows the structure of an organometallic compound which can be prepared according to the invention in perspective view, as obtained by means of X-ray structural analysis.

The present invention relates to a process for the preparation of organometallic compounds of transition metals containing optionally tetrahydrogenated 2-indenyl as a first ligand of the formula
wherein

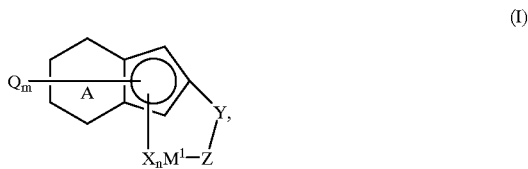

(I)

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenylphosphoryl or phenyl-$C_1$–$C_4$-alkyl-phosphoryl, m represents an integer in the range from 0 to 6, $M^1$ is a transition metal from sub-group IV, V or VI of the periodic system of the elements (Mendeleyev), X represents an anion, n is a number from zero to four, which is given by the valency and the bond state of $M^1$, Y represents a bridge from the group —C($R^1R^2$)—, —Si($R^1R^2$)—, —Ge($R^1R^2$)—, —C($R^1R^2$)—C($R^3R^4$)—, —C($R^1R^2$)—Si($R^3R^4$)— and —Si($R^1R^2$)—Si($R^3R^4$)—, wherein $R^1$, $R^2$, $R^3$ and $R^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group comprising open-chained and cyclic, optionally anionic π-systems, —N($R^5$)—, —P($R^6$)—, |N($R^5R^7$)—, |P($R^6R^8$)—, —O—, —S—, |O$R^5$— and |S$R^5$—, wherein the vertical line to the left of the element symbol N, P, O or S represents an electron pair and the bond between X and $M^1$ is of ionic, covalent or coordinate character and wherein each of $R^5$, $R^6$, $R^7$ and $R^8$, independently of the others, has the range of meanings given for $R^1$ to $R^4$, and $R^5$ and $R^7$ may additionally represent —Si($R^1R^2R^3$) and $R^6$ and $R^8$ may additionally represent —Si($R^1R^2R^3$), —O$R^1$, —S$R^1$ or —N($R^1R^2$), which process is characterized in that an optionally substituted 2-haloindene of the formula

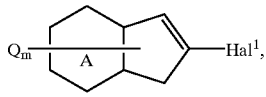

(II)

wherein $Hal^1$ represents Cl, Br or I and A, Q and m are as defined above, is reacted at a temperature of from $-20°$ C. to $+120°$ C. with elemental Mg or Zn in an amount of from 1 to 100 g-atoms of Mg or Zn per mole of (II) and, after separation of unreacted Mg or Zn, is reacted with a dihalide of the bridge Y of the formula

(III), wherein $Hal^2$ and $Hal^3$ are each independently of the other Cl, Br or I, and Y has the range of meanings given above, in an amount of from 1 to 20 moles of (III) per mole of (II), with removal of $MgHal^1Hal^2$ or $ZnHal^1Hal^2$, it being possible, when Y represents $-Si(R^1R^2)-$, $-Ge(R^1R^2)-$ or $-Si(R^1R^2)-Si(R^3R^4)-$, for the reactions of (II) with (i) Mg or Zn and (ii) with (III) also to be carried out simultaneously, and the reaction product of the formula

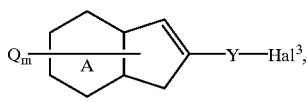

(IV)

wherein A, Q, m, Y and $Hal^3$ are as defined above, optionally after isolation, is reacted with a Z-derivative of the formula

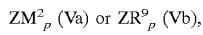

$ZM^2_p$ (Va) or $ZR^9_p$ (Vb), wherein $M^2$ represents Li, Na, K or $-MgHal^4$, wherein $Hal^4$ has the range of meanings given for $Hal^2$, p represents the number one or two, $R^9$ represents hydrogen, $-Si(R^1R^2R^3)$ or $Sn(R^1R^2R^3)$, and Z, $R^1$, $R^2$ and $R^3$ are as defined above, with removal of a compound of the formula $M^2 Hal^3$ (VIa) or $R^9 Hal^3$ (VIb), wherein $M^2$, $R^9$ and $Hal^3$ are as defined above, optionally in the presence of an auxiliary base, to form the 2-indenyl compound of the formula

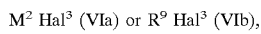

(VII)

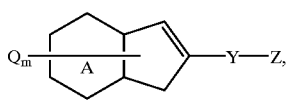

wherein A, Q, m, Y and Z are as defined above and which may be in the form of a dianion and wherein Z may further carry $M^2$, $R^9$ or an electron pair, and is then reacted further with a transition metal compound of the formula

$M^1X_q$ (VIII), wherein $M^1$ and X are as defined above, and q is a number from two to six, which is given by the oxidation number of $M^1$.

The invention relates also to the organometallic compounds, which can be prepared by means of the mentioned process, of transition metals containing optionally tetrahydrogenated 2-indenyl as a first ligand of the formula

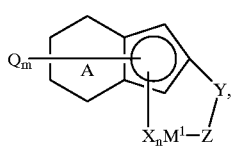

(I)

wherein

A represents the benzo system or the tetrahydrocyclohexyl system,

Q as the substituent of the optionally tetrahydrogenated 2-indenyl system represents $C_1-C_4$-alkyl, $C_6-C_{14}$-aryl, $C_7-C_{10}$-aralkyl, $C_1-C_4$-alkoxy, $C_1-C_4$-alkylthio, phenoxy, phenylthio, di-$C_1-C_4$-alkyl-amino, $C_6-C_{14}$-aryl-$C_1-C_4$-alkyl-amino, di-$C_6-C_{14}$-aryl-amino, dibenzylamino, tri-$C_1-C_4$-alkyl-silyl, di-$C_1-C_4$-alkyl-boranyl, phenyl-$C_1-C_4$-alkyl-boranyl, diphenylboranyl, di-$C_1-C_4$-alkyl-phosphoryl, diphenyl-phosphoryl or phenyl-$C_1-C_4$-alkyl-phosphoryl, m represents an integer in the range from 0 to 6, $M^1$ is a transition metal from sub-group IV, V or VI of the periodic system of the elements (Mendeleyev), X represents an anion, n is a number from zero to four, which is given by the valency and the bond state of $M^1$, Y represents a bridge from the group $-C(R^1R^2)-$, $-Si(R^1R^2)-$, $-Ge(R^1R^2)-$, $-C(R^1R^2)-C(R^3R^4)-$, $-C(R^1R^2)-Si(R^3R^4)-$ and $-Si(R^1R^2)-Si(R^3R^4)-$, wherein $R^1$, $R^2$, $R^3$ and $R^4$ are each independently of the others hydrogen, halogen, straight-chained or branched $C_1-C_{10}$-alkyl, $C_5-C_8$-cycloalkyl, $C_6-C_{14}$-aryl or $C_7-C_{10}$-aralkyl, and Z is a second ligand from the group comprising open-chained and cyclic, optionally anionic π-systems, $-N(R^5)-$, $-P(R^6)-$, $|N(R^5R^7)-$, $|P(R^6R^8)-$, $-O-$, $-S-$, $|OR^5-$ and $|SR^5-$, wherein the vertical line to the left of the element symbol N, P, O or S represents an electron pair and the bond between Z and $M^1$ is of ionic, covalent or coordinate character and wherein each of $R^5$, $R^6$, $R^7$ and $R^8$, independently of the others, has the range of meanings given for $R^1$ to $R^4$, and $R^5$ and $R^7$ may additionally represent $-Si(R^1R^2R^3)$ and $R^6$ and $R^8$ may additionally represent $-Si(R^1R^2R^3)$, $-OR^1$, $-SR^1$ or $-N(R^1R^2)$, with the exception of the compounds ethylene-bis(2-indenyl)-titanium dichloride, dimethylsilyl-(1-indenyl)(2-indenyl)-bis-dimethylamino-hafnium, dimethylsilyl-(1-indenyl)(2-indenyl)-dimethylhafnium, dimethyl-bis(2-indenyl)-silane-zirconium di-chloride, 1-cyclopentadienyl-2-(2-indenyl)-ethane-zirconium chloride, bis-(2-indenyl)-methane-zirconium dichloride, ethylene- 1-((3-but-3-enyl)inden-1-yl)-²-((1-but-3-enyl)-inden-2-yl)zirconium dichloride and ethylene-1-((3-allyldimethylsilyl)-inden-1-yl)-2-((1-allyldimethylsilyl)-inden-2-yl)zirconium dichloride.

The process according to the invention is characterized by a reaction sequence via the intermediate of formula (IV) above. Such intermediates have hitherto not been known. The invention therefore relates also to those intermediates.

The invention relates further to a process for the preparation of the intermediates of formula (IV), which is characterized in that an optionally substituted 2-haloindene of the formula

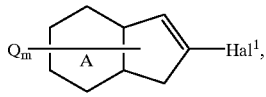
(II)

wherein

Hal¹, A, Q and m are as defined above, is reacted at a temperature of from −20° C. to +120° C. with elemental Mg or Zn in an amount of from 1 to 100 g-atoms of Mg or Zn per mole of (II) and, after separation of unreacted Mg or Zn, is reacted with a dihalide of Y of the formula

(III), wherein

Y, Hal² and Hal³ are as defined above, in an amount of from 1 to 20 moles of (III) per mole of (II), with removal of MgHal¹Hal² or ZnHal¹Hal², it being possible, when Y represents —Si(R¹R²)—, —Ge(R¹R²)— or —Si(R¹R²)—Si(R³R⁴)—, for the reactions of (II) with (i) Mg or Zn and (ii) with (III) also to be carried out simultaneously.

The invention relates also to the use of the compounds according to formula (I) as catalysts, both on a catalyst carrier (e.g. Al₂O₃, SiO₂ and other inert materials) and without a carrier, for the polymerization of monomers from the group comprising C₂–C₆-α-olefins, C₄–C₆-diolefins and cyclo(di)olefins or for the copolymerization of several of the mentioned monomers, especially for the preparation of amorphous, largely atactic polymers.

FIG. 1 shows the structure of an organometallic compound which can be prepared according to the invention in perspective view, as obtained by means of X-ray structural analysis, using the compound tert-butylamido-2-indenyl-dimethylsilyl-titanium dichloride as an example.

The invention relates preferably to the described process and to the compounds of formula (I) which can be prepared using that process and in which Y represents —Si(R¹R²)—, —Ge(R¹R²)— or —Si(R¹R²)—Si(R³R⁴)—, especially —Si(R¹R²)—, and the reactions of (II) with (i) Mg or Zn and (ii) with (III) to form the reaction product (IV) are carried out simultaneously.

Open-chained and cyclic π-systems within the scope of the meaning of Z are, for example, butadiene, isoprene, chloroprene, substituted or unsubstituted cyclopentadiene, substituted or unsubstituted 1-indene, substituted or unsubstituted 2-indene, substituted or substituted fluorene, which are bonded to the bridge Y in a covalent manner and to M¹ in an ionic, covalent or coordinate manner. Substituents of the π-systems may, independently of Q, have the range of meanings given for Q and, independently of m, likewise be present m times. Preference is given to the cyclic π-systems mentioned, especially to 2-indenyl.

The invention relates preferably to the process according to the invention and to non-C2-symmetrical organometallic compounds of transition metals of formula (1) according to the invention in which there is present, however, instead of Z the second ligand Z', which represents substituted or unsubstituted cyclopentadiene, substituted or unsubstituted 1-indene, unsubstituted 2-indene, substituted or unsubstituted fluorene, —N(R⁵)—, —P(R⁶)—, |N(R⁵R⁷)—, |P(R⁶R⁸)—, —O—, —S—, |OR⁵—or |SR⁵—, wherein R⁵ to R⁸ and the vertical lines are as defined above, and wherein the compounds of formula (I) according to the invention do not include the compounds ethylene-bis(2 -indenyl)-titanium dichloride, dimethylsilyl-(1-indenyl)(2-indenyl)-bis-dimethyl-amino-hafnium, dimethylsilyl-(1-indenyl)(2-indenyl)-dimethylhafnium, dimethyl-bis(2-indenyl)-silane-zirconium dichloride, 1-cyclopentadienyl-2-(2-indenyl)-ethane-zirconium chloride, bis-(2-indenyl)-methane-zirconium dichloride, ethylene-i-((3-but-3-enyl)inden-1-yl)-2-((1-but-3-enyl)-inden-2-yl)zirconium dichloride and ethylene-1-((3-allyldimethylsilyl)-inden-1-yl)-2-((1-allyldimethylsilyl)-inden-2-yl)zirconium dichloride.

Other preferred second ligands are those of the formula Z'' with the range of meanings substituted or unsubstituted 1-indenyl, substituted or unsubstituted fluorenyl, substituted or unsubstituted cyclopentadienyl, —N(R⁵)— or |N(R⁵R⁷)—, especially in conjunction with Y=—Si(R¹R²)— and M¹=Ti or Zr.

The non-C2-symmetrical compounds according to formula (I) are preferably used for the preparation of atactic polymers. Compounds of formula (I) wherein Y=—Si(R¹R²)—, M¹=Ti or Zr and Z=—N(R⁵)— are suitable especially for the preparation of atactic polypropylene.

Within the scope of the given meaning of A, the first ligand in (I) represents 2-indenyl or 2-tetrahydroindenyl, preferably 2-indenyl.

Straight-chained or branched C₁–C₁₀-alkyl is, for example, methyl, ethyl, propyl, isopropyl, butyl, isobutyl, tert-butyl, the isomers of pentyl, hexyl, octyl or decyl. Special preference is given to C₁–C₄-alkyl, especially methyl and ethyl.

C₅–C₈-Cycloalkyl is, for example, cyclopentyl, methyl-cyclopentyl, dimethyl-cyclopentyl, cyclohexyl, methyl-cyclohexyl, dimethyl-cyclohexyl, cycloheptyl, cyclooctyl, preferably cyclopentyl and cyclohexyl and their methyl and dimethyl derivatives.

C₆–C₁₄-Aryl is, for example, phenyl, naphthyl, biphenylyl, anthryl, phenanthryl, preferably phenyl.

C₇–C₁₀-Aralkyl is, for example, benzyl, α- or β-phenyl-ethyl, phenyl-propyl or phenyl-butyl.

C₁–C₄-Alkoxy and C₁–C₄-alkylthio are, for example, methoxy, methylthio, ethoxy, ethylthio, propoxy, propylthio, isopropoxy, isopropylthio, butoxy, butylthio, isobutoxy and isobutylthio.

Aryl and the aromatic moieties of aralkyl may be mono- or di-substituted by identical or different substituents selected from fluorine, chlorine, bromine, methyl, ethyl, methoxy and ethoxy.

Halogen within the scope of R¹ to R⁸ is, for example, fluorine, chlorine, bromine or various thereof, preferably chlorine.

M¹ is, for example, Ti, Zr, Hf, V, Nb, Ta, Cr, W, Mo, preferably Ti, Zr, Hf, V, Nb, especially Ti, Zr, Hf, more especially Ti, Zr. M¹ may be used either in the highest possible oxidation state or in a different, lower oxidation state and thus be present in the organometallic compounds. In many cases it is advantageous first to use M¹ in a lower oxidation state and then to oxidize to a higher state using a mild oxidizing agent, for example PbCl₂.

X is a mono- or multi-charged anion from the group chloride, bromide, iodide, C₁–C₄-carboxylate, amide, C₁–C₄-alkyl, phenyl, benzyl, neopentyl and butadienyl, preferably chloride or bromide; it is also possible for various of the mentioned anions to be present.

Hal¹, Hal² and Hal³ within the scope of (II) and (III) are each independently of the others Cl, Br or I; preferably, Hal¹ is Br and Hal² and Hal³ are Cl or Br.

The temperature for the reaction of (II) with Mg or Zn is in the range of from −20° C. to +120° C., preferably from 0° C. to +100° C., especially from +25° C. to +80° C.

The amount of Mg or Zn is from 1 to 100 g-atoms per mole of (II). It is in principle also possible to work with amounts that are outside the mentioned range. With less than 1 g-atom of Mg or Zn per mole of (II), the reaction of (II) is incomplete, and with more than 100 g-atoms no further advantage in respect of the completeness and speed of the reaction is to be expected. There are preferably used from 1 to 10 g-atoms of Mg or Zn, especially from 1 to 5 g-atoms of Mg or Zn, per mole of (II). Of the metals Mg and Zn, Mg is preferred for the reaction.

The temperature for the further reaction with (III) is likewise in the range of from −20° C. to +120° C., preferably from 0° C. to +100° C., especially from +25° C. to +80° C.

The amount of (III) is from 1 to 20 moles per mole of (II). With regard to amounts outside that range, the comments made above in respect of the amount of Mg or Zn apply. There are preferably used from 1 to 10 moles of (III), especially from 1 to 2 moles of (III), per mole of (II).

Unreacted Mg or Zn and (III) are separated off from the reaction batch in a manner known to the person skilled in the art and can be used again.

The process according to the invention may be carried out in the presence of a polar, aprotic solvent. Suitable solvents are, for example, methylene chloride, chloroform, dimethylformamide, N-methyl-pyrrolidone and ethers; of those solvents, preference is given to the ethers, for example diethyl ether, diisopropyl ether, dioxane, tetrahydrofuran and other ethers known to the person skilled in the art. The amount of solvent is so chosen that (II) and the organo-Mg or organo-Zn compound resulting therefrom are present in solution and the unreacted Mg or Zn can be separated off, for example, by filtration or decantation or analogous separating methods. That amount is, for example, from 50 to 1000 % of the amount of (II).

Y is preferably —C($R^1R^2$)—, —Si($R^1R^2$)—, especially —Si($R^1R^2$)—.

Where Y represents —Si($R^1R^2$)—, —Ge($R^1R^2$)— or —Si($R^1R^2$)—Si($R^3R^4$)—, the simultaneous reaction of (II) with (i) Mg or Zn and (ii) with (III) opens up an elegant possibility of saving one reaction step.

Where the reaction of (IV) with (Va) or (Vb) to form (VII) is carried out in the presence of an auxiliary base, suitable auxiliary bases are, for example: open-chained or cyclic tertiary aliphatic amines having a total of from 3 to 30 carbon atoms, such as trimethylarnine, triethylamine, tripropylamine, triisopropylamine, tributylamine, triisobutylamine, trihexylamine, trioctylamine, tridecylamine, N-methyl-piperidine, N,N'-dimethyl-piperazine, diaza-bicyclo-nonane (DBN), diaza-bicyclo-octane (DABCO), diazabicyclo-undecane (DBU), also amines having carbon chains of different lengths, such as N,N-dimethyl-butylamine, N,N-dimethyl-octylamine, N,N-dimethyl-stearylamine and the like, and aromatic amines, such as pyridine, methyl-pyridine, quinoline, N,N-dimethyl-aniline and the like.

The reaction mixture containing the organometallic compound (I) is worked up by means of operations known to the person skilled in the art, such as filtration, removal of volatile portions of the mixture by distillation, chromatography and crystallization.

The organometallic compounds of formula (I) can be used as catalysts for the (co)polymerization of $C_2$—$C_6$-α-olefins, $C_4$–$C_6$-diolefins, cyclo(di)olefins or mixtures of several thereof. Monomers of the mentioned groups are, for example: ethylene, propylene, butylene, pentene, hexene and their branched isomers, 1,3-butadiene, 1,3- or 1,4-pentadiene, 1,3-, 1,4- or 1,5-hexadiene, isoprene, chloroprene, norbornene, ethylidene-norbornene and vinyl-norbornene.

For (co)polymerization, the compounds of formula (I) are frequently used in combination with co-catalysts.

Suitable co-catalysts are the co-catalysts that are known in the field of metallocenes, such as polymeric or oligomeric alumoxanes, Lewis acids and aluminates and borates. In this connection reference is made especially to Macromol. Symp. Vol. 97, July 1995, p. 1–246 (for alumoxanes), as well as to EP 277,003, EP 277,004, Organometallics 1997, 16, 842–857 (for borates) and EP 573,403 (for aluminates).

Especially suitable co-catalysts are methylalumoxane, methylalumoxane modified by triisobutylaluminium (TIBA), as well as diisobutylalumoxane, trialkylaluminium compounds, such as trimethylaluminium, triethylaluminium, triisobutylaluminium, triisooctyl-aluminium, also dialkylaluminium compounds, such as diisobutylaluminium hydride, diethylaluminium chloride, substituted triarylboron compounds, such as tris(pentafluorophenyl)borane, and also ionic compounds that contain tetrakis(pentafluorophenyl) borate as anion, such as triphenyl-methyltetrakis(pentafluorophenyl) borate, trimethylammonium tetrakis(pentafluorophenyl) borate, N,N-dimethylanilinium tetrakis(pentafluoro-phenyl) borate, substituted triarylaluminium compounds, such as tris(pentafluorophenyl)aluminum, as well as ionic compounds that contain tetrakis(pentafluorophenyl) aluminate as anion, such as triphenylmethyltetrakis(pentafluorophenyl) aluminate, N,N-dimethylanilinium tetrakis(pentafluorophenyl) aluminate.

It is, of course, possible to use the co-catalysts in mixtures with one another. The most advantageous mixing ratios for a particular case are to be determined by means of suitable preliminary experiments.

Such (co)polymerizations are carried out in the gas, liquid or slurry phase. The temperature range therefore is from −20° C. to +200° C., preferably from 0° C. to 160° C., especially from +20° .C to +80° C.; the pressure range is from 1 to 50 bar, preferably from 3 to 30 bar. Solvents that are used concomitantly are, for example, saturated aliphatic compounds or (halo)aromatic compounds, such as pentane, hexane, heptane, cyclohexane, petroleum ether, petroleum, hydrogenated benzine, benzene, toluene, xylem, ethylbenzene, chlorobenzene and the like. Those reaction conditions for the (co)polymerization are in principle known to the person skilled in the art.

Important polymers that can be prepared using the organometallic compounds according to the invention as catalysts are polymers of propylene and copolymers thereof. Suitable as comonomers are $C_2$- to $C_{10}$-alkenes, such as ethylene, 1-butene, 1-pentene, 1-hexene, 1-octene, isobutylene, and arylalkenes, such as, for example, styrene. Suitable comonomers are also conjugated dienes, such as 1,3-butadiene, isoprene, 1,3-pentadiene, and unconjugated dienes, such as 1,4-hexadiene, 1,5-heptadiene, 5,7-dimethyl-1,6-octadiene, 4-vinyl-1-cyclohexene, 5-ethylidene-2-norbornene, 5-vinyl-2-norbornene and dicyclopentadiene.

The propylene (co)polymers that can be prepared in that manner have molecular weights of $M_w$>100 000 g/mol. and molecular weight distributions of $M_w/M_n$<4. The propylene (co)polymers have intrinsic viscosities greater than 1 dl/g. The crystallinities are less than 10%, wherein % crystallinity=(enthalpy of fusion/209 J/g)×100 and the enthalpy of fusion in J/g is determined by means of the DSC method. Special preference is given to propylene (co)polymers having enthalpies of fusion with a value of less than 5 J/g (DSC method). The propylene (co)polymers are readily soluble in common solvents, such as hexane, heptane, diethyl ether or toluene.

In the manner described it is possible to prepare especially also rubbers based on propylene and one or more of the mentioned comonomers. Special preference is given to the copolymerization of ethylene and propylene, yielding amorphous propylene (co)polymers having an ethylene content in the polymer in the range of from 1 to 70 wt. %, preferably from 10 to 65 wt. %.

In the manner described it is also possible to prepare EPDM rubbers based on ethylene, propylene and a diene, especially 5-ethylidene-2-norbornene. The EPDM rubbers are characterized in that they have high molecular weights and low crystalline contents.

For example, the (co)polymerization of propylene can be carried out with or without the mentioned comonomers as follows: a steel autoclave is filled after the conventional purification operations with a solvent and a scavenger, for example triisobutylaluminium. The scavenger renders harmless any possible impurities and catalyst poisons, e.g. water or other oxygen-containing compounds. A compound of formula (I) is then added as the catalyst precursor. The reactor is subsequently filled with monomers to a given pressure and set at a selected temperature, and polymerization is started by the addition of one or more of the above-mentioned co-catalysts. The polymerization may take place in a continuous or discontinuous process.

EXAMPLES

The invention is explained in greater detail with reference to the Examples which follow.

General information: The preparation and handling of organometallic compounds were carried out with the exclusion of air and moisture with argon protection (Schlenk technique). All the required solvents were rendered absolute prior to use by boiling for several hours over a suitable drying agent and subsequent distillation under argon. The compounds were characterized by $^1$H-NMR, $^{13}$C-NMR and mass spectroscopy.

Polymer Characterization

Intrinsic viscosity was determined in an Ubbelohde capillary viscometer at 140° C. in o-dichlorobenzene as solvent (multipoint measurement). Molecular mass distribution was determined in an apparatus called the WATERS 150 CV plus Gel Permeation Chromatograph at 140° C. in o-dichlorobenzene. DSC measurements were carried out on an apparatus from Perkin-Elmer called the Differential-Scanning-Calorimeter DSC-2 in accordance with the following procedure: two heatings −90° C. to +180° C., rate of heating 20 K/min., rapid cooling at 320 K/min. to −90° C., flushing with nitrogen, weighed-in amounts 12.3 mg of sample composition in standard capsules. The Mooney viscosity was determined in accordance with ASTM 1646 / DIN 53 523. Determination of the polymer composition by IR spectroscopy was carried out in accordance with ASTM D 3900.

Example 1

Preparation of chloro-2-indenyldimethylsilane

2-Bromoindene (4.0 g, 0.02 mol.) was dissolved in 4 ml of tetrahydrofuran and added dropwise to a mixture consisting of magnesium (0.73 g, 0.03 mol.) and dichlorodimethylsilane (5.0 g, 0.04 mol.) in 4 ml of tetrahydrofuran. During the addition, the solution boiled slightly. After 15 hours' stirring, the volatile constituents were removed under an oil pump vacuum, and 40 ml of n-pentane were added to the residue. The resulting magnesium salt was filtered off with suction. The solvent was removed under an oil pump vacuum to yield 4.6 g (95%) of chloro-2-indenyl-dimethylsilane in the form of a colorless oil.

$^1$H NMR (CDCl$_3$): δ7.3–7.6 (m, 4 H, ind.), 7.29 (s, 1 H, ind.), 3.65 (s, 2 H, CH$_2$), 0.74 (s, 6 H, SiMe$_2$).

$^{13}$C NMR (CDCl$_3$): δ146.4 ($C_{ind.}$, [C—Si]), 144.6 ($C_{ind.}$, [C]), 143.2 (CH═CSi), 126.3 (arom. CH, ind.), 125.6 (arom. CH, ind.), 123.70 (arom. CH, ind.), 121.8 (arom. CH, ind.), 41.5 (CH$_2$), 2.0 (SiMe).

Example 2

Preparation of cyclopentadienyl-2-indenyl-dimethylsilane

Chloro-2-indenyldimethylsilane (4.6 g, 0.022 mol.) from Example 1 was dissolved in 20 ml of diethyl ether. The solution was cooled to 0° C., and a solution of cyclopentadienylsodium (1.94 g, 0.022 mol.) in 20 ml of tetrahydrofuran was added dropwise. The mixture was stirred for 15 hours at 25° C. 50 ml of water were then added, and the organic phase was washed with water again and dried over Na$_2$SO$_4$. After removal of the solvents under an oil pump vacuum, the light-yellow oil that remained was purified by means of column chromatography. The solvent was removed to yield 2.4 g (46%) of cyclopentadienyl-2-indenyl-dimethylsilane in the form of a colorless oil.

$^1$H NMR (CDCl$_3$): δ7.6–7.3 (m, 4 H, arom. H), 7.01 (s, 1 H, Ph—CH═C(SiMe$_2$Cp)), 6.72 (m, 4 H, Cp), 3.56 (s, 2 H, CH$_2$, ind.), {3.67, 3.49, 3.18} (s, 1 H, CH—Si, Cp), {0.57, 0.51, 0.26} (s, 6 H, Si—(CH$_3$)$_2$).

$^{13}$C NMR (CDCl$_3$): δ146.5 (C), 145.1 (C), 141.8 (Ph—CH═C(SiMe$_2$Cp)), 137.9 (Ph—C(SiMe$_2$Cp)═CH), 132.9 (broad, CH, Cp), 130.5 (broad, CH, Cp), 126.2 (CH, ind.), 124.9 (CH, ind.), 123.5 (CH, ind.), 120.9 (CH, ind.), 51.1 (broad, CH—Si, Cp), 45.3 (broad, CH—Si, Cp), 42.6 (CH$_2$, ind.), −3.9 (SiMe).

Example 3

Preparation of cyclopentadienyl-2-indenyl-dimethylsilylzirconium dichloride

Cyclopentadienyl-2-indenyl-dimethylsilane (1.0 g, 0.0042 mol.) from Example 2 was dissolved in 10 ml of tetrahydrofuran and 10 ml of diethyl ether and reacted at −40° C. with a 2.5 molar solution of n-BuLi in hexane (3.5 ml, 0.0084 mol.). Stirring was carried out for 15 hours at 25° C. The solvents were then removed under an oil pump vacuum and the residue was washed with 20 ml of petroleum ether. The dilithium salt so purified was suspended in a further 20 ml of petroleum ether. ZrCl$_4$.2 THF (1.58 g, 0.042 mol.) was likewise suspended in 20 ml of toluene and added in one portion to the dilithium salt at 25° C. After 30 minutes, a yellowish orange discoloration became noticeable, which increasingly deepened. After 15 hours' stirring, the solvents were removed under an oil pump vacuum and the residue was extracted with 80 ml of toluene and freed of insoluble constituents by filtration over kieselguhr. The toluene was removed under an oil pump vacuum. 1.08 g (64%) of cyclopentadienyl-2-indenyl-dimethylsilylzirconium dichloride were obtained in the form of a yellowish orange solid.

$^1$H NMR (CDCl$_3$): δ7.63 (dd, 2 H, $^2J_{HH}$=3.0, 5.0 Hz, ind.), 7.30 (dd, 2 H. $^2J_{HH}$3.0, 5.0 Hz, ind.), 6.90 (pt, 2 H, $^2J_{HH}$=0.9 Hz, Cp), 6.16 (s, 2 H, ind.), 6.05 (pt, 2 H, $^2J_{HH}$0.9 Hz, Cp), 0.83 (s, 6H, SiMe$_2$).

Example 4

Preparation of a Solution of Lithium Fluorene

Fluorene (2.2 g, 0.0136 mol.) was dissolved in 40 ml of diethyl ether and reacted at 0° C. with a 2.5 molar solution of n-BuLi in hexane (5.5 ml, 0.0136 mol.). After 4 hours' stirring at 25° C., the volume of the solution was reduced to half under an oil pump vacuum.

Example 5

Preparation of fluorenyl-2-indenyl-dimethylsilane

A solution of lithium fluorene from Example 4 was slowly added dropwise at 0° C., by means of a septum and a syringe, to a solution of chloro-2-indenyl-dimethylsilane (2.85 g, 0.0136 mol.) according to Example 1 in 20 ml of diethyl ether. After 2 hours' stirring at 25° C., the resulting LiCl was filtered off. The solvent was removed from the filtrate and the beige-colored residue was dissolved in hot ether/petroleum ether and crystallized at −30° C. 3.45 g (75%) of fluorenyl-2-indenyldimethylsilane were obtained in the form of a colorless solid. M.p.: 125° C.

$^1$H NMR (CDCl$_3$): δ7.9–7.8 (m, 2 H, arom. H), 7.5–7.2 (m, 12 H, arom. H), 7.04 (s, 1 H, ind.), 4.10 (s, 1 H, CH, flu.), 3.29 (s, 1 H, CH$_2$, ind.), 0.20 (s, 6 H, SiMe$_2$).

$^{13}$C NMR (CDCl$_3$): δ147.4 (C$_{ind.}$, [C]), 146.0 (C$_{ind.}$, [C]), 146.0 (C$_{ind.}$, [C—Si]), 145.7 (C$_{flu.}$, [C]), 143.2 (CH═CSi), 141.1 (C$_{flu.}$, [C]), 126.8 (CH, arom.$^1$), 126.6 (CH, arom.), 125.9 (CH, arom.), 125.5 (CH, arom.), 124.7 (CH, arom.), 124.2 (CH, arom.), 121.6 (CH, arom.), 120.5 (CH, arom.), 43.4 (CHSi, flu.), 46.5 (CH$_2$, ind.), −3.4 (SiMe$_2$).

Example 6

Preparation of fluorenyl-2-indenyl-dimethylsilylzirconium dichloride

Fluorenyl-2-indenyldimethylsilane (1.33 g, 0.004 mol.) from Example 5 was dissolved in a mixture of 10 ml of tetrahydrofuran and 30 ml of diethyl ether and reacted at −40° C. with a 2.5 molar solution of n-BuLi in hexane (3.2 ml, 0.008 mol.). Stirring was carried out for 15 hours at 25° C. The solvents were then removed under an oil pump vacuum and the residue was washed with 20 ml of petroleum ether. The dilithium salt so purified was suspended in a further 20 ml of petroleum ether. ZrCl$_4$ (0.815 g, 0.0035 mol.) was suspended in 20 ml of petroleum ether and added to the dilithium salt at 25° C. After 15 hours' stirring, the solvents were removed under an oil pump vacuum and the residue was extracted with 80 ml of CH$_2$Cl$_2$ and freed of insoluble constituents by filtration over kieselguhr. The CH$_2$Cl$_2$ was evaporated off under an oil pump vacuum. 1.90 g (95%) of the title compound were obtained in the form of an orange-colored solid.

$^1$H NMR (CDCl$_3$): δ8.15 (d, 2 H, $^3J_{HH}$=2 Hz, arom.), 7.70 (d, 2 H, $^3J_{HH}$=2 Hz, arom.), 7.6 (m, 2 H, ind.), 7.4–7.1 (m, 6 H, arom.), 6.05 (s, 2 H, 2-ind.), 1.21 (s, 6 H, SiMe$_2$).

Example 7

Preparation of trimethylsilylcyclopentadienyl-2-indenyl-dimethylsilane

Chloro-2-indenyldimethylsilane (5.15 g, 0.025 mol.) according to Example 1 was dissolved in 10 ml of tetrahydrofuran. The solution was cooled to 0° C. and a solution of trimethylsilylcyclopentadienyllithium (3.60 g, 0.025 mol.) in 20 ml of tetrahydrofuran was added. Stirring was carried out for 15 hours at 25° C. 50 ml of water were then added, and the organic phase was washed with water again and dried over Na$_2$SO$_4$. After removal of the solvents under an oil pump vacuum, the yellowish oil that remained was purified by means of column chromatography. The solvents were removed to yield 2.12 g (34%) of trimethylsilylcyclopentadienyl-2-indenyl-dimethylsilane in the form of a colorless oil.

$^1$H NMR (CDCl$_3$): δ7.6–7.4 (m, 2 H, arom. H), 7.3–7.2 (m, 2 H, arom. H), 7.14 (s, 1 H, ind.), 6.77 (pt, 2 H, $^3J$=0.5 Hz, Cp), 6.68 (pt, 2 H, $^3J$=0.5 Hz, Cp), 3.42 (s, 2 H, CH$_2$, ind.), 0.26 (s, 6 H, SiMe$_2$), −0.06 (s, 9 H, SiMe$_3$).

$^{13}$C NMR (CDCl$_3$): δ147.2 (C$_{ind.}$, [C]), 146.6 (C$_{ind.}$, [C]), 145.1 C$_{ind.}$, [C—Si]), 141.8 (CH═CSi, ind.), 135.7 (CH, Cp), 130.9 (CH, Cp), 126.6 (CH, arom., ind.), 124.7 (CH, arom., ind.), 123.4 (CH, arom., ind.), 120.8 (CH, arom., ind.), 43.4 (CH$_2$, ind.), 39.1 (C═CSi$_2$, Cp), −0.9 (SiMe$_3$), −1.9 (SiMe$_2$).

Example 8

Preparation of trimethylsilylcyclopentadienyl-2-indenyl-dimethylsilylzirconium dichloride Trimethylsilylcyclopentadienyl-2-indenyl-dimethylsilane (0.931 g, 0.003 mol.) from Example 7 was dissolved in 30 ml of diethyl ether and reacted at −40° C. with a 2.5 molar solution of n-BuLi in hexane (2.4 ml, 0.006 mol.). Stirring was carried out for 15 hours at 25° C. The solvents were then removed under an oil pump vacuum and the residue was washed with 20 ml of petroleum ether. The dilithium salt so purified was suspended in a further 20 ml of petroleum ether. ZrCl$_4$ (0.815 g, 0.0035 mol.) was likewise suspended in 40 ml of petroleum ether and added to the dilithium salt at 25° C. After 15 hours' stirring, the solvents were removed under an oil pump vacuum and the residue was extracted with 80 ml of methylene chloride and freed of insoluble constituents by filtration over kieselguhr. The methylene chloride was evaporated off under an oil pump vacuum. 0.747 g (53%) of the title compound was obtained in the form of a light-yellow solid. M.p.: 85° C.

$^1$H NMR (CDCl$_3$): 7.70 (d, 1 H, $^3J_{HH}$=2.0 Hz, ind.), 7.47 (d, 1H, $^3J_{HH}$=2.0 Hz, ind.), 7.3 (m, 2 H, ind.), 7.06 (s, 1 H, ind.), 6.33 (pt, 1 H, $^3J_{HH}$=0.5 Hz, Cp), 6.17 (pt, 1 H, $^3J_{HH}$=0.5 Hz, Cp), 6.15 (pt, 1 H, $^3J_{HH}$=0.5, Cp), 6.02 (s, 1 H, ind.), 0.86 (s, 3 H, SiMe), 0.77 (s, 3 H, SiMe), 0.23 (s, 9 H, SiMe$_3$).

$^{13}$C NMR (CDCl$_3$): δ150.0 (C), 135.8 (CH), 135.3 (C), 131.4 (C), 126.8 (CH), 126.0 (CH), 125.1 (CH), 125.0 (CH), 122.3 (CH), 116.4 (CH), 112.2 (C), 110.7 (C), 109.6 (CH), 101.7 (CH), −0.39 (SiMe$_3$), −3.9 (SiMe), −5.9 (SiMe).

Example 9

Preparation of 1-indenyl-2-indenyl-dimethylsilane

Chloro-2-indenyldimethylsilane (4.95 g, 0.023 mol.) according to Example 1 was dissolved in 20 ml of diethyl ether. The solution was cooled to 0° C., and a solution of lithium indene (1.94 g, 0.022 mol.) in 25 ml of diethyl ether was added dropwise. The mixture was stirred for 2 hours at 25° C. and then heated to reflux. For working up, 60 ml of water were added and the organic phase was washed with water again and dried over Na$_2$SO$_4$. After removal of the solvents under an oil pump vacuum, the light-yellow oil that remained was purified by means of column chromatography. 3.23 g (47%) of 1-indenyl-2-indenyl-dimethylsilane were obtained in the form of a colorless oil which crystallized in the refrigerator at 4° C. M.p.: 45° C.

$^1$H NMR (CDCl$_3$): δ7.9–7.8 (m, 2 H, ind.), 7.7–7.5 (m, 2 H, ind.), 7.48 (s, 1 H, ind.), 7.35 (d, 1 H, $^3$J=2.0 Hz, ind.), 7.03 (d, 1 H, $^3$J=2.0 Hz, ind.), 4.06 (s, 1 H, CH), 3.69 (s, 1 H, CH$_2$), 3.64 (s, 1 H, CH$_2$), 0.58 (s, 3 H, SiMe$_2$), 0.52 (s, 3 H, SiMe$_2$).

$^1$C NMR (CDCl$_3$): δ147.5 (C$_{ind.}$[C]), 146.6 (C$_{ind.}$, [C]), 146.0 (C$_{ind.}$, [C]), 145.7 (C$_{ind.}$, [C]), 145.7 (C$_{ind.}$, [C]), 143.2 (CH=CSi), 136.2 (CH=CSi), 130.2 (CH=CSi), 127.2 (arom. CH, ind.), 125.9 (arom. CH, ind.), 124.6 (arom. CH, ind.), 124.5 (arom. CH, ind.), 124.5 (arom. CH, ind.), 123.7 (arom. CH, ind.), 121.9 (arom. CH, ind.), 121.9 (arom. CH, ind.), 46.5 (CH—Si), –2.9 (SiMe), –3.27 (SiMe).

Example 10

Preparation of 1-indenyl-2-indenyl-dimethylsilylzirconium dichloride

The compound 1-indenyl-2-indenyldimethylsilane (1.0 g, 0.0035 mol.) from Example 9 was dissolved in a mixture of 5 ml of tetrahydrofuran and 30 ml of diethyl ether and reacted at –40° C. with a 2.5 molar solution of n-BuLi in hexane (2.8 ml, 0.007 mol.). Stirring was carried out for 15 hours at 25° C. The solvents were then removed under an oil pump vacuum and the residue was washed with 20 ml of petroleum ether. The dilithium salt so purified was suspended in a further 20 ml of petroleum ether. ZrCl$_4$ (0.815 g, 0.0035 mol.) was likewise suspended in 20 ml of toluene and added to the dilithium salt at 25° C. After 15 hours' stirring, the solvents were removed under an oil pump vacuum and the residue was extracted with 80 ml of CH$_2$Cl$_2$ and freed of insoluble constituents by filtration over kieselguhr. The CH$_2$Cl$_2$ was evaporated off under an oil pump vacuum. 1.59 g (96%) of 1-indenyl-2-indenyldimethylsilylzirconium dichloride were obtained in the form of an orange-colored solid.

$^1$H NMR (CDCl$_3$): δ7.6–7.5 (m, 2 H, ind.), 7.4–7.3 (m, 2 H, ind.), 7.2–7.1 (m, 4 H, ind.), 7.01 (d, 1 H, $^3$J$_{HH}$=0.75 Hz, 1-ind.), 6.20 (d, 1 H, $^3$J$_{HH}$=0.75 Hz, 1-ind.), 6.20 (d, 1 H, $^3$J$_{HH}$=0.75 Hz, 1-ind.), 6.13 (s, 1 H, 2-ind.), 6.10 (s, 1 H, 2-ind.), 1.11 (s, 3 H, SiMe), 0.89 (s, 3 H, SiMe).

$^{13}$C NMR (CDCl$_3$): δ135.3 (C), 133.8 (C), 131.3 (C), 127.5 (CH), 126.6 (CH), 126.4 (CH), 126.2 (CH), 125.3 (CH), 124.8 (CH), 124.4 (CH), 120.0 (CH), 118.1 (CH), 110.2 (C), 107.1 (CH), 103.8 (CH), 91.78 (C), –2.4 (SiMe), –4.6 (SiMe).

Example 11

Preparation of the Catalyst Solution 18.1 g (40 μmol.) of 1-indenyl-2-indenyl-dimethylsilylzirconium dichloride from Example 10 were dissolved in 19 ml of toluene; 1 ml of methylalumoxane (MAO in toluene from Witco) was added and pre-activation was carried out for 20 minutes at 20° C.

Polymerization of Ethylene 500 ml of toluene and 5 ml of methylalumoxane (MAO in toluene from Witco) were placed into a 1.4 liter steel autoclave. The solution was brought to a temperature of 40° C. Ethylene was then metered in until the internal pressure of the reactor rose to 7 bar. Polymerization was started by the addition of 0.5 ml of the catalyst solution (=1 μmol. of 1-indenyl-2-indenyl-dimethylsilylzirconium dichloride). After a polymerization time of 15 minutes at 40° C. and 7 bar, the pressure in the autoclave was relieved and the polymer was filtered off, washed several times with methanol and dried for 20 hours in vacuo at 60° C. 13.2 g of polyethylene were obtained.

Example 12

Polymerization of Propylene 100 ml of toluene and 5 ml of a 10% solution of methylalumoxane (MAO in toluene from Witco) were placed into a 250 ml glass reactor and heated to 40° C. Propylene was then introduced continuously into the solution at a pressure of 1.1 bar by means of a gas inlet pipe. Polymerization was started by the addition of 5 ml of the pre-activated catalyst solution from Example 11 (=10 μmol. of 1-indenyl-2-indenyl-dimethylsilylzirconium dichloride). At a temperature of 40° C. and a propylene pressure of 1.1 bar, there was obtained after a polymerization time of one hour a clear reaction solution, which was stopped by the addition of 100 ml of methanol. The resulting elastic polymer was filtered off, washed with methanol and dried in a vacuum drying cabinet. 12.2 g of solid amorphous polypropylene were obtained.

Example 13 (Comparison Example)

The polymerization of Example 12 was repeated with the difference that, instead of 1-indenyl-2-indenyl-dimethylsilylzirconium dichloride, dimethylsilyl-bis(1-indenyl)zirconium dichloride in the form of the racemate was used as the catalyst component. Polypropylene was formed as a white precipitate even during the polymerization. 13.4 g of crystalline polypropylene powder having a melting point of 145° C. were obtained.

Example 14

Preparation of tert-butylamine-2-indenyl-dimethylsilane

Chloro-2-indenyldimethylsilane (4.7 g, 0.02 mol.) according to Example 1 was dissolved in 20 ml of diethyl ether and added to a solution of tert-BuNH$_2$ (10 ml, 0.2 mol.) in 50 ml of diethyl ether at 25° C. A suspension formed. After 12 hours' stirring, the solvent was removed under an oil pump vacuum and the residue was taken up in 40 ml of n-pentane. Tert-BuNH$_2$.HCl that formed was separated off by filtration. The n-pentane was removed to yield 5.2 g (97%) of tert-butylamine-2-indenyl-dimethylsilane in the form of a colorless oil.

$^1$H NMR (CDCl$_3$): δ7.5–7.4 (m, 2 H, ind.), 7.3–7.2 (m, 2 H, ind.), 7.18 (s, 1 H, ind.), 3.52 (s, 2 H, CH$_2$), 1.20 (s, 9 H, C(CH$_3$)$_3$), 0.78 (s, broad, NH), 0.32 (s, 6 H, SiMe$_2$).

$^{13}$C NMR (CDCl$_3$): δ151.0 (C$_{ind.}$, [C—Si]), 146.9 (C$_{ind.}$, [C]), 145.8 (C$_{ind.}$, [C]), 140.9 (CH=CSi), 126.2 (arom. CH, ind.), 124.7 (arom. CH, ind.), 123.7 (arom. CH, ind.), 120.9 (arom. CH, ind.), 49.5 (C(CH$_3$)$_3$), 42.3 (CH$_2$), 33.7 (C(CH$_3$)$_3$), 1.1 (SiMe).

Example 15

Preparation of tert-butylamido-2-indenyl-dimethylsilylzirconium dichloride

Tert-butylamine-2-indenyl-dimethylsilane (1.5 g, 0.0061 mol.) from Example 14 was dissolved in 30 ml of diethyl ether, and 5.0 ml of a solution of n-BuLi in hexane (2.5 molar) was added dropwise at −30° C. During the addition, a colorless suspension formed, which was stirred for 15 hours at 25° C. The diethyl ether was then evaporated off in vacuo and the salt that remained was washed twice with 30 ml of n-pentane each time and suspended again in 20 ml of n-pentane. ZrCl$_4$ (1.41 g, 0.006 mol.) in 40 ml of toluene was added to that suspension at 25° C. During the addition of ZrCl$_4$ the reaction solution rapidly turned yellowish orange. The mixture was stiffed for 15 hours. Working up was carried out by removal of the solvent under an oil pump vacuum and extraction with 70 ml of CH$_2$Cl$_2$. 0.72 g (29%) of tert-butylamido-2-indenyl-dimethylsilyl-zirconium dichloride was obtained in the form of a yellow powder.

$^1$H NMR (CDCl$_3$): δ7.74–7.71 (dd, $^3J_{HH}$=1.0 Hz, 1.5 Hz, 2 H, ind.), 7.42–7.39 (dd, $^3J_{HH}$=1.0 Hz, 1.5 Hz, 2 H, ind.), 6.70 (s, 2 H, ind.), 1.38 (s, 9 H, C(CH$_3$)$_3$), 0.67 (s, 9H, SiMe$_2$).

$^{13}$C NMR (CDCl$_3$): δ134.2 (C), 128.1 (CH), 123.4 (CH), 119.7 (CH), 114.6 (C—Si), 65.2 (C(CH$_3$)$_3$), 32.8 (C(CH$_3$)$_3$), 0.85 (Si—CH$_3$).

Example 16

Preparation of the Catalyst Solution 13.6 mg (33.5 μmol.) of tert-butylamido-2-indenyl-dimethylsilylzirconium dichloride from Example 15 were dissolved in a mixture of 0.9 ml of triisobutylaluminium and 15.9 ml of hexane.

Polymerization of Ethylene 500 ml of hexane, 0.1 ml of triisobutylaluminium and 2.5 ml of the catalyst solution (=5 μmol. of tert-butylamido-2-indenyldimethylsilyl-zirconium dichloride) were placed into a 1.4 liter steel autoclave. The solution was brought to a temperature of 40° C. Ethylene was then metered in until the internal pressure of the reactor rose to 7 bar. Polymerization was started by the addition of a solution of 4.6 mg (5 μmol.) of triphenylmethyl-tetrakis(pentafluorophenyl) borate in 5 ml of toluene. After a polymerization time of 10 minutes at 40° C. and 7 bar, the pressure in the autoclave was relieved and the polymer was filtered off, washed several times with methanol and dried for 20 hours in vacuo at 60° C. 10.1 g of polyethylene were obtained.

Example 17

Preparation of the Catalyst Solution 17.2 mg (42.4 μmol.) of tert-butylamido-2-indenyldimethylsilyl-zirconium dichloride from Example 15 were dissolved in 20.2 ml of toluene and pre-activated with 1 ml of a 10% solution of methylaluminoxane (MAO in toluene from Witco). Copolymerization of ethylene and propylene 100 ml of toluene and 5 ml of a 10% solution of methylalumoxane (MAO in toluene from Witco) were placed into a 250 ml glass reactor. An ethylene/propylene mixture (weight ratio 1:2) was then introduced continuously into the solution at 20° C. and a pressure of 1.1 bar by means of a gas inlet pipe. Polymerization was started by the addition of 0.5 ml of the pre-activated catalyst solution (=1 μmol. of tert-butylamido-2-indenyl-dimethylsilylzirconium dichloride). At a temperature of 20° C. and under a pressure of 1.1 bar, there was obtained after a polymerization time of one hour a clear reaction solution, which was stopped by the addition of 100 ml of methanol. The resulting elastic polymer was filtered off, washed with methanol and dried in a vacuum drying cabinet. 2.3 g of amorphous copolymer were obtained. Determination of the composition of the copolymer by means of IR spectroscopy revealed a content of 63.7 wt. % ethylene and 36.3 wt. % propylene.

Example 18

Preparation of tert-butylamido-2-indenyl-dimethylsilyltitanium dichloride

Tert-butylamine-2-indenyl-dimethylsilane (1.0 g, 0.0041 mol.) from Example 14 was dissolved in 20 ml of n-pentane, and 3.4 ml of a solution of n-BuLi in hexane (2.5 molar) were added dropwise at 0° C. During the addition, a suspension formed, which conglomerated into a resinous composition after 15 hours' stirring. The n-pentane was evaporated off in vacuo and the yellowish powder that remained was dissolved at −78° C. in 20 ml of tetrahydrofuran and transferred by means of a cannula to a suspension of TiCl$_3$. 3 THF in 10 ml of tetrahydrofuran at −78° C, during which a deep yellow discoloration was observed. When room temperature had been reached, solid PbCl$_2$ (1.13 g, 0.0041 mol.) was added and stirring was carried out for 0.5 hour. The suspension then turned reddish brown. The solvent was removed and the powder that remained was extracted three times with 20 ml of toluene each time. After adding toluene and stirring for a short time, the suspension was allowed to precipitate and the supernatant liquid was removed by means of a pipette. The toluene was then removed from the extract and replaced by n-pentane, yielding 1.06 g (71.9%) of tert-butylamido-2-indenyldimethylsilyl-titanium dichloride in the form of a reddish brown solid. By means of crystallization from methylene chloride at −30° C. it was possible to obtain single crystals. An X-ray structural analysis was carried out (FIG. 1). M.p.: 143° C.

$^1$H NMR (CDCl$_3$): δ7.74–7.71 (dd, $^3J_{HH}$=1.0 Hz, 1.5 Hz, 2 H, ind.), 7.42–7.39 (dd $^3J_{HH}$=1.0 Hz, 1.5 Hz, 2 H, ind.), 6.78 (s, 2 H, ind.), 1.41 (s, 9 H, C(CH$_3$)$_3$), 0.77 (s,6 H, SiMe$_2$).

$^{13}$C NMR (CDCl$_3$): δ134.2 (C), 128.1 (CH), 124.4 (CH), 119.7 (CH), 114.6 (C—Si), 65.2 (C(CH$_3$)$_3$), 32.3 (C(CH$_3$)$_3$), 0.0 (Si—CH$_3$).

Example 19

Preparation of the Catalyst Solution 27 mg (74.5 μmol.) of tert-butylamido-2-indenyl-dimethylsilyltitanium dichloride from Example 17 were dissolved in a mixture of 1.9 ml of triisobutylaluminium and 13 ml of hexane.

Polymerization of Ethylene

The polymerization of Example 16 was repeated with the difference that 5 μmol. of tert-butylamido-2-indenyl-dimethylsilyltitanium dichloride (=1 ml of the catalyst solution) were used as the catalyst component instead of tert-butylamido-2-indenyl-dimethylsilylzirconium dichloride. 12.1 g of polyethylene were obtained.

Example 20

Polymerization of Propylene 500 ml of hexane, 0.1 ml of triisobutylaluminium (TIBA) and 1 ml of the catalyst solution from Example 19 (=5 μmol. of tert-butylamido-2-indenyl-dimethylsilyltitanium dichloride) were placed into a 1.4 liter steel autoclave. The autoclave was then filled with propylene until a pressure of 2.0 bar had become established. The temperature was then brought to 20° C. Polymerization was started by the addition of a solution of 18.5 mg (20 μmol.) of triphenylmethyl-tetrakis(pentafluorophenyl) borate in 10 ml of toluene. Propylene was metered in continuously so that the pressure in the autoclave remained constant at 2.0 bar. After a polymerization time of 50 minutes at 20° C., the reaction was stopped with 500 ml of methanol and the resulting polymer was filtered off and dried for 20 hours in vacuo at 60° C. 68.9 g of atactic polypropylene were obtained. GPC analysis revealed: $M_w$=159 000 g/mol., $M_w/M_n$=2.28. Analysis by $^{13}$C-NMR spectroscopy gave the following composition: % mm=19.1 (isotactic portion); % (mr/rm)=50.8 (atactic portion); % rr=30.0 (syndiotactic portion); according to the DSC measurement, the polymer is completely amorphous. The enthalpy of fusion was zero J/g. Using the DSC method, a Tg of −19° C. was determined.

Example 21

Copolymerization of Ethylene and Propylene 500 ml of hexane and 0.1 ml of TIBA were placed into a 1.4 liter steel autoclave equipped with a mechanical stirrer, a manometer, a temperature sensor, a temperature-control device, a catalyst transfer tube and monomer metering devices for ethylene and propylene. 1 ml of the catalyst solution from Example 20 (=5 μmol. of tert-butylamido-2-indenyl-dimethylsilyltitanium dichloride) was added thereto. The internal temperature was set at 20° C. using a thermostat. 15 g of ethylene and 90 g of propylene were then metered in. Polymerization was started by the addition of a solution of 9.22 mg (10 μmol.) of triphenylmethyl-tetrakis (pentafluorophenyl) borate in 5 ml of toluene. In semi-batch operation, ethylene and propylene were metered in continuously in a weight ratio of 15:85 so that the internal pressure at 20° C. remained constant at 5 bar. After a polymerization time of 30 minutes, the polymer was precipitated with methanol, isolated and dried for 20 hours at 60° C. in vacuo, yielding 44 g of copolymer. Determination of the composition of the copolymer by means of IR spectroscopy revealed a content of 9.9 wt. % ethylene and 90.1 wt. % propylene. According to the DSC measurement, the copolymer is completely amorphous. The enthalpy of fusion was zero J/g. Using the DSC method, a Tg of −28° C, was determined.

Example 22

Copolymerization of Ethylene and Propylene

The polymerization of Example 21 was repeated with the difference that 21.3 g of propylene and 22.0 g of ethylene were placed into the autoclave and ethylene and propylene were metered in continuously in a weight ratio of 50:50. The polymerization time was 70 minutes. 57.2 g of an amorphous copolymer having an ethylene content of 49.9 wt. % and a propylene content of 50.1 wt. % (IR spectroscopy) were obtained. Measurement of the intrinsic viscosity gave a value of 2.59 dl/g. Determination of the Mooney value gave: ML (1+4) 125° C.=112.

Example 23

Copolymerization of Ethylene and Propylene

The polymerization of Example 21 was repeated with the difference that 35.3 g of propylene and 14.9 g of ethylene were placed into the autoclave and ethylene and propylene were metered in continuously in a weight ratio of 30:70. The polymerization time was 120 minutes. 94 g of an amorphous copolymer having an ethylene content of 27.9 wt. % and a propylene content of 72.1 wt. % (IR spectroscopy) were obtained. Measurement of the intrinsic viscosity gave a value of 2.50 d/g. Determination of the Mooney value gave: ML (1+4) 125° C.=107.

Example 24

Terpolymerization of ethylene, propylene and 5-ethylidene-2-norbornene (ENB)

The polymerization of Example 23 was repeated with the difference that 45.6 g of propylene and 19.8 g of ethylene and 5 ml of ENB were placed into the autoclave and ethylene and propylene were metered in continuously in a weight ratio of 30:70. The polymerization time was 90 minutes. 80.2 g of an amorphous terpolymer having an ethylene content of 24.7 wt. %, a propylene content of 71.6 wt. % and an ENB content of 3.81 wt. % (IR spectroscopy) were obtained. Measurement of the intrinsic viscosity gave a value of 2.56 dl/g. Determination of the Mooney value gave: ML (1+4) 125° C.=123. Using the DSC method, a Tg of −36° C. was determined (melt enthalpy=0 J/g).

Example 25

Terpolymerization of Ethylene, propylene and 5-ethylidene-2-norbornene (ENB)

The polymerization of example 22 was repeated with the difference that 21.3 g of propylene and 22.0 g of ethylene and 5 ml of ENB were placed into the autoclave and ethylene and propylene were metered in continuously in a weight ratio of 50:50. The polymerization time was 80 minutes. 67 g of an amorphous terpolymer having an ethylene content of 47.3 wt.-% of ethylene, 48.0 wt.-% of propylene and 4.9 wt.-% of ENB(IR spectroscopy) were obtained. Measurement of the intrinsic viscosity gave a value of 2.26 dl/g. Determination of the Mooney value gave: ML (1+4) 125° C.=133. Using the DSC method, a Tg of −51° C. was determined (melt enthalpy=0 J/g).

Example 26

Terpolymerization of Ethylene, propylene and 5-ethylidene-2-norbornene (ENB)

The polymerization of Example 22 was repeated with the difference that 12.8 g of propylene and 18.6 g of ethylene and 5 ml of ENB were placed into the autoclave and ethylene and propylene were metered in continuously in a weight ratio of 60:40. The polymerization time was 90 minutes. 56.3 g of an amorphous terpolymer having an ethylene content of 56.6 wt.-% of ethylene, 37.3 wt.-% of propylene and 6.5 wt.-% of ENB (IR spectroscopy) were obtained. Measurement of the intrinsic viscosity gave a value of 2.64 dl/g. Using the DSC-method, a Tg of −47° C. was determined (melt enthalpy=12.6 J/g).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of organometallic compounds of transition metals containing optionally tetrahydrogenated 2-indenyl as a first ligand of the formula

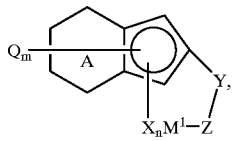

(I)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_4$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenyl-phosphoryl or phenyl-$C_1$–$C_4$-alkyl-phosphoryl, m represents an integer in the range from 0 to 6, $M^1$ is a transition metal from sub-group IV, V or VI of the periodic system of the elements (Mendeleyev), X represents an anion, n is a number from zero to four, which is given by the valency and the bond state of $M^1$, Y represents a bridge from the group —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— and —$Si(R^1R^2)$—$Si(R^3R^4)$—, wherein $R^1$, $R^2$, $R^3$ and $R^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Z is a second ligand from the group comprising open-chained and cyclic, optionally anionic π-systems, —$N(R^5)$—, —$P(R^6)$—, $|N(R^5R^7)$—, $|P(R^6R^8)$—, —O—, —S—, $|OR^5$— and $|SR^5$—, wherein the vertical line to the left of the element symbol N, P, O or S represents an electron pair and the bond between Z and $M^1$ is of ionic, covalent or coordinate character and wherein each of $R^5$, $R^6$, $R^7$ and $R^8$, independently of the others, has the range of meanings given for $R^1$ to $R^4$, and $R^5$ and $R^7$ may additionally represent —$Si(R^1R^2R^3)$ and $R^6$ and $R^8$ may additionally represent —$Si(R^1R^2R^3)$, —$OR^1$, —$SR^1$ or —$N(R^1R^2)$, wherein said process comprises the steps of reacting an optionally substituted 2-haloindene of the formula

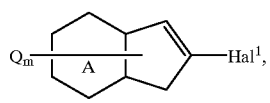

(II)

wherein $Hal^1$ represents Cl, Br or I and A, Q and m are as defined above, is reacted at a temperature of from −20° C. to +120° C. with elemental Mg or Zn in an amount of from 1 to 100 g-atoms of Mg or Zn per mole of (II) and, after separation of unreacted Mg or Zn, with a dihalide of the bridge Y of the formula $$Hal^2\text{—}Y\text{—}Hal^3 \quad (III),$$

wherein $Hal^2$ and $Hal^3$ are each independently of the other Cl, Br or I, and Y has the range of meanings given above, in an amount of from 1 to 20 moles of (III) per mole of (II), with removal of $MgHal^1Hal^2$ or $ZnHal^1Hal^2$; and when Y represents —$Si(R^1R^2)$—, —$Ge(R^1R^2)$— or —$Si(R^1R^2)$—$Si(R^3R^4)$—, to optionally simultaneously react (II) with (i) Mg or Zn and (ii) with (III) to form a reaction product of the formula

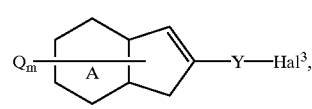

(IV)

wherein A, Q, m, Y and $Hal^3$ are as defined above; and optionally, after isolation, reacting said reaction product (IV) with a Z-derivative of the formula $$ZM^2_p \text{ (Va) or } ZR^9_p \text{ (Vb)},$$

wherein $M^2$ represents Li, Na, K or —$MgHal^4$, wherein $Hal^4$ has the range of meanings given for $Hal^2$, p represents the number one or two, $R^9$ represents hydrogen, —$Si(R^1R^2R^3)$ or $Sn(R^1R^2R^3)$, and Z, $R^1$, $R^2$ and $R^3$ are as defined above, with removal of a compound of the formula $$M^2Hal^3 \text{ (VIa) or } R^9Hal^3 \text{ (VIb)},$$

wherein $M^2$, $R^9$ and $Hal^3$ are as defined above, optionally in the presence of an auxiliary base, to form the 2-indenyl compound of the formula

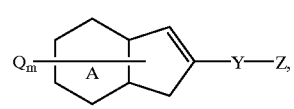

(VII)

wherein A, Q, m, Y and Z are as defined above and which may be in the form of a dianion and wherein Z may further carry $M^2$, $R^9$ or an electron pair, and is then reacted further with a transition metal compound of the formula $$M^1X_q \quad (VIII),$$

wherein $M^1$ and X are as defined above, and q is a number from two to six, which is given by the oxidation number of $M^1$.

2. A process according to claim 1, characterized in that Y is a bridge from the group —$Si(R^1R^2)$—, —$Ge(R^1R^2)$— and —$Si(R^1R^2)$—$Si(R^3R^4)$—, and the reactions of (II) with (i) Mg or Zn and (ii) with (III) to form the reaction product are carried out simultaneously.

3. A process according to claim 1, characterized in that $M^1$ is a transition metal from the group Ti, Zr, Hf, V, Nb.

4. A process according to claim 3, characterized in that $M^1$ is a transition metal from the group Ti, Zr, Hf.

5. A process according to claim 4, characterized in that $M^1$ is a transition metal from the group Ti, Zr.

6. A process according to claim 1, characterized in that from 1 to 10 g-atoms of Mg or Zn are used per mole of (II) and from 1 to 10 moles of (III) are used per mole of (II).

7. An non-C2-symmetrical mono-cyclopentadienyl organometallic compound of a transition metal containing optionally substituted 2-indenyl as a first ligand of the formula

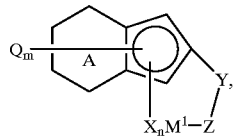

(I)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenylphosphoryl or phenyl-$C_1$–$C_4$-alkyl-phosphoryl, m represents an integer in the range from 0 to 6, $M^1$ is a transition metal from sub-group IV, V or VI of the periodic system of the elements (Mendeleyev), X represents an anion, n is a number from zero to four, which is given by the valency and the bond state of $M^1$, Y represents a bridge from the group —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— and —$Si(R^1R^2)$—$Si(R^3R^4)$—, wherein $R^1$, $R^2$, $R^3$ and $R^4$ are each independently of the others hydrogen, halogen, straight-chained or branched $C_1$–$C_{10}$-alkyl, $C_5$–$C_8$-cyclo-alkyl, $C_6$–$C_{14}$-aryl or $C_7$–$C_{10}$-aralkyl, and Z is a second ligand from the group comprising openchained and cyclic, optionally anionic π-systems, —$N(R^5)$—, —$P(R^6)$—, $|N(R^5R^7)$—, $|P(R^6R^8)$—, —O—, —S—, $|OR^5$— and $|SR^5$—, wherein the vertical line to the left of the element symbol N, P, O or S represents an electron pair and the bond between Z and $M^1$ is of ionic, covalent or coordinate character and wherein each of $R^5$, $R^6$, $R^7$ and $R^8$, independently of the others, has the range of meanings given for $R^1$ to $R^4$, and $R^5$ and $R^7$ may additionally represent —Si$(R^1R^2R^3)$ and $R^6$ and $R^8$ may additionally represent—Si$(R^1R^2R^3)$, —$OR^1$, —$SR^1$ or —$N(R^1R^2)$, with the exception of the compounds ethylene-bis(2-indenyl)-titanium dichloride, dimethylsilyl-(1-indenyl)(2-indenyl)-bis-dimethylamino-hafnium, dimethylsilyl-(1-indenyl)(2-indenyl)-dimethylhafnium, dimethyl-bis(2-indenyl)-silanezirconium dichloride, 1-cyclopentadienyl-2-(2-indenyl)-ethane-zirconium chloride, bis-(2-indenyl)-methane-zirconium dichloride, ethylene-1-((3-but-3-enyl)inden-1-yl)-2-((1-but-3-enyl)-inden-2-yl)zirconium dichloride and ethylene-1-((3-allyldimethylsilyl)-inden-1-yl)-2-((1-allyldimethylsilyl)-inden-2-yl)zirconium dichloride.

8. A non-C2-symmetrical organometallic compound of a transition metal according to claim 7, wherein in formula (I) there is present instead of Z the second ligand Z', which represents substituted or unsubstituted cyclopentadiene, substituted or unsubstituted 1-indene, unsubstituted 2-indene, substituted or unsubstituted fluorene, —$N(R^5)$—, —$P(R^6)$—, $|N(R^5R^7)$—, $|P(R^6R^8)$—, —O—, —S—, $|OR^5$— or $|SR^5$—, wherein $R^5$ to $R^8$ and the vertical lines are as defined in claim 7, with the exception of the compounds ethylene-bis(2-indenyl)-titanium dichloride, dimethylsilyl-(1-indenyl)(2-indenyl)-bis-dimethylaminohafnium, dimethylsilyl-(1-indenyl)(2-indenyl)-dimethylhafnium, dimethyl-bis(2-indenyl)-silane-zirconium dichloride, 1-cyclopentadienyl-2-(2-indenyl)-ethane-zirconium chloride, bis-(2-indenyl)-methane-zirconium dichloride, ethylene-1-((3-but-3-enyl)inden-1-yl)-2-((1-but-3-enyl)-inden-2-yl)zirconium dichloride and ethylene-1-((3-allyldimethylsilyl)-inden-1-yl)-2-(( 1-allyldimethylsilyl)-inden-2-yl)zirconium dichloride.

9. A non-C2-symmetrical organometallic compound of a transition metal according to claim 8, wherein in formula (I) there is present instead of Z' the second ligand Z'', which represents substituted or unsubstituted 1-indenyl, substituted or unsubstituted fluorenyl, substituted or unsubstituted cyclopentadienyl, —$N(R^5)$— or $|N(R^5R^7)$—, and wherein, furthermore, in formula (I) Y is —$Si(R^1R^2)$— and $M^1$ is Ti or Zr, wherein $R^1$, $R^2$, $R^5$ and $R^7$ and the vertical line next to the element symbol N are as defined in claim 7, with the exception of the compounds ethylene-bis(2-indenyl)-titanium dichloride, dimethylsilyl-(1-indenyl)(2-indenyl)-bis-dimethylamino-hafnium, dimethylsilyl-(1-indenyl)(2-indenyl)-dimethylhafnium, dimethyl-bis(2-indenyl)-silane-zirconium dichloride, 1-cyclopentadienyl-2-(2-indenyl)-ethane-zirconium chloride, bis-(2-indenyl)-methane-zirconium dichloride, ethylene-1-((3-but-3-enyl)inden-1-yl)-2-((1-but-3-enyl)-inden-2-yl)zirconium dichloride and ethylene-1-((3-allyldi-methylsilyl)-inden-1-yl)-2-((1-allyl-dimethylsilyl)-inden-2-yl)zirconium dichloride.

10. An intermediate of the formula

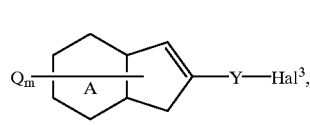

(IV)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenyl-phosphoryl or phenyl-$C_1$–C4-alkyl-phosphoryl, m represents the number zero, one or two, Y represents a bridge from the group —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— and —$Si(R^1R^2)$—$Si(R^3R^4)$—, wherein $R^1$, $R^2$, $R^3$ and $R^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Hal$^3$ is Cl, Br or I.

11. A process for the preparation of an intermediate of the formula

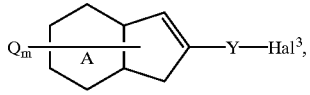

(IV)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenyl-phosphoryl or phenyl-$C_1$–$C_4$-alkyl-phosphoryl, m represents the number zero, one or two, Y represents a bridge from the group —C(R$^1$R$^2$)—, —Si(R$^1$R$^2$)—, —Ge(R$^1$R$^2$)—, —C(R$^1$R$^2$)—C(R$^3$R$^4$)—, —C(R$^1$R$^2$)—Si(R$^3$R$^4$)— and —Si(R$^1$R$^2$)—Si(R$^3$R$^4$)—, wherein R$^1$, R$^2$, R$^3$ and R$^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Hal$^3$ is Cl, Br or I, characterized in that an optionally substituted 2-haloindene of the formula

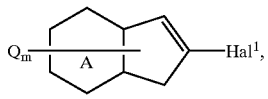

(II)

wherein

Hal$^1$, represents Cl, Br or I,

A, Q and m are as defined above, is reacted at a temperature of from −20° C. to +120° C. with elemental Mg or Zn in an amount of from 1 to 100 g-atoms of Mg or Zn per mole of (II) and, after separation of unreacted Mg or Zn, is reacted with a dihalide of the formula

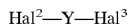 (III), wherein

Y is as defined above and

Hal$^2$ and Hal$^3$ are each independently of the other Cl, Br or I, in an amount of from 1 to 20 moles of (III) per mole of (II), with removal of MgHal$^1$Hal$^2$ or ZnHal$^1$Hal$^2$, it being possible, when Y represents —Si(R$^1$R$^2$)—, —Ge(R$^1$R$^2$)— or —Si(R$^1$R$^2$)—Si(R$^3$R$^4$)—, for the reactions of (II) with (i) Mg or Zn and (ii) with (III) also to be carried out simultaneously.

12. A process according to claim 1, wherein Y is a bridge from the group —Si(R$^1$R$^2$)—.

13. A non-C2-symmetrical organometallic compound of a transition metal, wherein said organic metallic compound is tert-butylamine-2-indenyl-dimethylsilyltitanium dichloride.

14. A non-C2-organometallic compound of a transition metal containing optionally substituted 2-indenyl as a first ligand of the formula

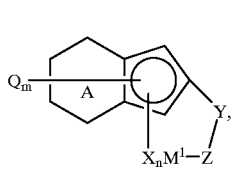

(I)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$–$C_4$-alkyl-boranyl, phenyl-$C_1$–$C_4$-alkyl-boranyl, diphenylboranyl, di-$C_1$–$C_4$-alkyl-phosphoryl, diphenylphosphoryl or phenyl-$C_1$–$C_4$-alkyl-phosphoryl, m represents the number zero, one or two, M$^1$ is a transition metal from sub-group IV, V or VI of the periodic system of the elements (Mendeleyev), X represents an anion, n is a number from zero to four, which is given by the valency and the bond state of M$^1$, Y represents a bridge from the group —C(R$^1$R$^2$)—, —Si(R$^1$R$^2$)—, —Ge(R$^1$R$^2$)—, —C(R$^1$R$^2$)—C(R$^3$R$^4$)—, —C(R$^1$R$^2$)—Si(R$^3$R$^4$)— and —Si(R$^1$R$^2$)—Si(R$^3$R$^4$)—, wherein R$^1$, R$^2$, R$^3$ and R$^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Z is a second ligand selected from the group consisting of substituted or unsubstituted fluorenyl.

15. An organometallic compound of a transition metal containing optionally substituted 2-indenyl as a first ligand of the formula

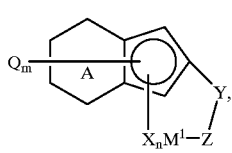

(I)

wherein

A represents the benzo system or the tetrahydrocyclohexyl system,

Q as the substituent of the optionally tetrahydrogenated 2-indenyl system represents $C_1$–$C_4$-alkyl, $C_6$–$C_{14}$-aryl, $C_7$–$C_{10}$-aralkyl, $C_1$–$C_4$-alkoxy, $C_1$–$C_4$-alkylthio, phenoxy, phenylthio, di-$C_1$–$C_4$-alkyl-amino, $C_6$–$C_{14}$-aryl-$C_1$–$C_4$-alkyl-amino, di-$C_6$–$C_{14}$-aryl-amino, dibenzylamino, tri-$C_1$–$C_4$-alkyl-silyl, di-$C_1$C$_4$-alkyl-boranyl, phenyl-$C_1$–$C_4$-alkyl-boranyl, diphenylboranyl, di-$C_1$–$C_4$-alkyl-phosphoryl, diphenylphosphoryl or phenyl-$C_1$–$C_4$alkyl-phosphoryl, m represents the number zero, one or two, M$^1$ is a transition metal from sub-group IV, V or VI of the periodic system of the elements (Mendeleyev), X represents an anion, n is a number from zero to four, which is given by the valency and the bond state of $M^1$, Y represents a bridge from the group —$C(R^1R^2)$—, —$Si(R^1R^2)$—, —$Ge(R^1R^2)$—, —$C(R^1R^2)$—$C(R^3R^4)$—, —$C(R^1R^2)$—$Si(R^3R^4)$— and —$Si(R^1R^2)$—$Si(R^3R^4)$—, wherein $R^1$, $R^2$, $R^3$ and $R^4$ are each independently of the others hydrogen, halogen, straight-chained or branched $C_1$–$C_{10}$-alkyl, $C_5$–$C_8$-cycloalkyl, $C_6$–$C_{14}$-aryl or $C_7$–$C_{10}$-aralkyl, and Z is a second ligand selected from the group consisting of substituted or unsubstituted 1-indenyl.

* * * * *